US012313532B1

(12) United States Patent
Xue et al.

(10) Patent No.: US 12,313,532 B1
(45) Date of Patent: May 27, 2025

(54) STATIC CONE PENETRATION TEST DEVICE AND TEST METHOD INCORPORATING HYPERSPECTRAL IMAGING TECHNOLOGY

(71) Applicant: Institute of Rock and Soil Mechanics, Chinese Academy of Sciences, Hubei (CN)

(72) Inventors: Qiang Xue, Hubei (CN); Houzhen Wei, Hubei (CN); Yong Wan, Hubei (CN); Xiaolong Ma, Hubei (CN); Hang Ruan, Hubei (CN); Xiang Sun, Hubei (CN); Jiangshan Li, Hubei (CN)

(73) Assignee: Institute of Rock and Soil Mechanics, Chinese Academy of Sciences, Hubei (CN)

( * ) Notice: Subject to any disclaimer, the term of this patent is extended or adjusted under 35 U.S.C. 154(b) by 0 days.

(21) Appl. No.: 18/796,276

(22) Filed: Aug. 6, 2024

(30) Foreign Application Priority Data

Nov. 29, 2023 (CN) .......................... 202311624717.9

(51) Int. Cl.
*G01N 21/31* (2006.01)
*E02D 1/00* (2006.01)
(Continued)

(52) U.S. Cl.
CPC ........... *G01N 21/3151* (2013.01); *E02D 1/00* (2013.01); *G01N 21/255* (2013.01); *G01N 33/24* (2013.01);
(Continued)

(58) Field of Classification Search
CPC .. G01N 21/3151; G01N 21/255; G01N 33/24; E02D 1/00
See application file for complete search history.

(56) References Cited

U.S. PATENT DOCUMENTS 5,902,939 A * 5/1999 Ballard ................. E21B 49/081
73/864.81
2022/0056800 A1 2/2022 Wright et al.

FOREIGN PATENT DOCUMENTS

CN 115928689 4/2023

OTHER PUBLICATIONS

Liu Qinghao et al., "Research progress of soil in-situ penetration technology and penetration mechanism", Optics and Precision Engineering, vol. 31 No. 5, with English translation thereof, Mar. 2023, pp. 588-620.

* cited by examiner

*Primary Examiner* — Rebecca C Bryant
(74) *Attorney, Agent, or Firm* — JCIP GLOBAL INC.

(57) ABSTRACT

The present disclosure relates to a static cone penetration test device. The device includes a housing, an optical window and a friction cylinder coaxially connected. Light sources are mounted in the optical window and a static cone penetration assembly is disposed in the friction cylinder to detect a resistance the device suffers when the device is pressed into soil. An optical fiber sensor, a wireless transceiver, a data processing chip and a power supply are disposed in the housing. The optical fiber sensor is used to receive the reflected light of a target object and output spatial position information and spectrum information. The wireless transceiver is used to upload test data and receive a control signal. The data processing chip is used to analyze the test data. The present disclosure has the advantages of compact structure, high spectral resolution, quick imaging speed, and strong immunity to interference.

10 Claims, 6 Drawing Sheets

(51) Int. Cl.
*G01N 21/25* (2006.01)
*G01N 33/24* (2006.01)
*G02B 6/26* (2006.01)
*G02B 6/32* (2006.01)

(52) U.S. Cl.
CPC .............. *G02B 6/26* (2013.01); *G02B 6/325* (2013.01); *G01N 2021/3155* (2013.01); *G01N 2201/1293* (2013.01)

STATIC CONE PENETRATION TEST DEVICE AND TEST METHOD INCORPORATING HYPERSPECTRAL IMAGING TECHNOLOGY

CROSS-REFERENCE TO RELATED APPLICATIONS

This application claims the priority benefit of China application no. 202311624717.9 filed on Nov. 29, 2023. The entirety of each of the above-mentioned patent applications is hereby incorporated by reference herein and made a part of this specification.

TECHNICAL FIELD

The present disclosure relates to the photoelectric field and the field of civil engineering test technologies, and in particular to a static cone penetration test device and test method incorporating hyperspectral imaging technology.

BACKGROUND

In the hyperspectral imaging technology, light with different wavelengths is differentiated by light-splitting element and imaged on an image sensor separately, so as to obtain image information of target objects with hundreds of spectral bands and create a three-dimensional data cube. By further analyzing the relationship between light intensity and light wavelength, chemical composition information of target objects within a region of interest can be obtained. The hyperspectral imaging technology has full-spectrum information capture capability within the ultraviolet, visible and near-infrared regions, and thus more substantial structure information can be obtained from the region of interest than the visible light observation. Therefore, it has significant advantages in the aspects such as soil mineral identification and pollutant detection and the like.

In a static cone penetration test, a standard probe is penetrated soil to obtain an end resistance, a lateral frictional resistance and a pore water pressure suffered by the probe during the penetration process, so as to determine multiple mechanical parameters of the soil such as a foundation bearing capacity, a shear strength and a single-pile bearing capacity and the like. Combined with regional experiences and adjacent test data, mechanical property evaluation of different soils and mechanical classification can be carried out.

However, it is impossible to obtain the mineral composition information of deep in-situ soils by the static cone penetration test and determine a soil type online, leading to inaccurate classification of complex thin soils. Furthermore, it is also impossible to obtain a type, a relative content and a spatial distribution of pollutants by the static cone penetration test. Therefore, it is necessary to develop a static cone penetration test device incorporating hyperspectral imaging technology to carry out in-situ detection on soils and obtain substance structure information and spectral information of minerals and pollutants in the soils online.

SUMMARY

In order to overcome the inability of the conventional static cone penetration test to obtain composition information of deep in-situ soils, the present disclosure provides a static cone penetration test device and test method incorporating hyperspectral imaging technology.

The static cone penetration test device incorporating hyperspectral imaging technology in the present disclosure employs the following technical solution.

A static cone penetration test device incorporating hyperspectral imaging technology, comprising:
a housing;
a friction cylinder, coaxially connected with the housing;
a static cone penetration assembly, disposed inside the friction cylinder to detect a resistance the device suffers when the device is pressed into a soil;
an optical window, coaxially connected with the friction cylinder;
light sources, mounted inside the optical window, wherein light emitted from the light sources reaches the surface of the soil after passing through the optical window, and a target object in the soil reflects the light and then the reflected light enters the housing through the optical window;
inside the housing are disposed:
an optical fiber sensor, configured to receive the reflected light of the target object and output information of two spatial dimensions and one spectral dimension;
a wireless transceiver, configured to upload test data and receive a control signal;
a data processing chip, configured to perform analysis processing on an electrical signal output by the optical fiber sensor and send data to the wireless transceiver; and
a power supply, configured to supply power to the light sources, the optical fiber sensor, the data processing chip and the wireless transceiver.

During detection, the present device penetrates soil by using a penetration device and a detection rod. During a static cone penetration process, light emitted by the light sources is penetrated through the optical window into the soil and irradiated on the target object and then reflected, and the optical fiber sensor receives the reflected light and outputs spatial position and spectrum information of the target object within a planar imaging region.

The present disclosure is compact in structure and easy to use in an integrated way in a confined space and also obtains, in real-time, hyperspectral images of the in-situ soil; on the other hand, by the spectral information, chemical composition information of the soil can be obtained and then compared with a result of the static cone penetration test to carry out analysis and verification, improving the accuracy of classifying complex soil using the static cone penetration test.

Furthermore, the static cone penetration assembly comprises a measurement rod disposed inside the friction cylinder and multiple resistance strain gauges fixedly connected on a circumferential side of the measurement rod; a conveying piece for conveying a force applied by the soil to the friction cylinder to the measurement rod is disposed inside the friction cylinder.

Furthermore, the measurement rod comprises an upper measurement rod, a middle-end head and a lower measurement rod fixedly connected coaxially, and the middle-end head has a larger diameter than the upper measurement rod and the lower measurement rod; the conveying piece is a fixing clamp ring, wherein an inner ring of the fixing clamp ring is fixedly connected at the middle-end head and an outer ring is fixedly connected on an inner sidewall of the friction cylinder; and the resistance strain gauges are mounted on circumferential sides of the upper measurement rod and the lower measurement rod.

Furthermore, a washer is disposed between the friction cylinder and the housing.

When the present device penetrates the soil, a force applied by the soil to the friction cylinder is conveyed to the measurement rod by a fixing clamp ring. The resistance of the resistance strain gauges changes depending on the deformation of the measurement rod, and thus the resistance can be converted into an electrical signal.

Furthermore, the optical fiber sensor comprises an optical fiber array, a splitter device, an area array optical fiber bundle and an area array image sensor connected in sequence, the optical fiber array is disposed on an inner side surface of the optical window, and an axial direction of the optical fiber array is perpendicular to the inner side surface of the optical window.

The light emitted by the light source is irradiated on the target object and then reflected and then penetrated through the optical window into the optical fiber array, and through the optical fiber array into the splitter device; the splitter device decomposes the composite light into discrete lights of different wavebands and the discrete lights are then transmitted into the area array image sensor through the area array optical fiber bundle for signal processing.

Furthermore, the area array image sensor comprises an optical fiber decoder and a charge coupling device; the optical fiber decoder is connected with an output end of the area array optical fiber bundle to decode an image encoding signal into a two-dimensional optical signal; the charge coupling device is connected with the optical fiber decoder to convert the decoded two-dimensional optical signal into an electrical signal, the charge coupling device comprises two spatial dimensions and one spectral dimension, wherein the spatial dimensions are used to output spatial position information of the target object within a planar imaging region and the spectral dimension is used to output spectrum information of the target object.

Furthermore, the splitter device comprises a splitter housing, an input fiber collimator, a directional splitter device and an output fiber collimator, wherein the input fiber collimator, the directional splitter device and the output fiber collimator are located in the splitter housing and sequentially disposed along a light path; the input fiber collimator, the directional splitter device and the output fiber collimator are coaxial.

The light sequentially passes through the input fiber collimator, the directional splitter device and the output fiber collimator, and the composite light is decomposed into discrete lights of different wavebands.

Furthermore, the directional splitter device is a composite structure of directional grating-prism-diffraction grating-prism and the directional grating regulates a diverging light into a parallel light, and the diffraction grating decomposes a composite light passing through the directional grating into discrete lights of different wavelengths.

Light adjustment and splitting are performed by a composite structure of directional grating-prism-diffraction grating-prism. The light path has a simple structure and there are no movable parts, increasing the immunity to vibration and interference.

Furthermore, a black light-absorbing coating is disposed of on the inner sidewall of the splitter housing.

The black light-absorbing coating and the stray-light-eliminating diaphragm can reduce non-imaging lights and improve the imaging effect.

The present disclosure further provides a static cone penetration test method incorporating hyperspectral imaging technology, which is carried out by using the above static cone penetration test device incorporating hyperspectral imaging technology. The method includes the following steps:

at step 1, performing device test and calibration and mounting resistance strain gauges;

at step 2, penetrating the device into the soil by using a detection rod and a penetration device;

at step 3, recording the depth of an end head of the device in real-time, detecting the resistance of the resistance strain gauges and calculating an end resistance and a lateral frictional resistance; further, transmitting in real-time, by the wireless transceiver, the hyperspectral images obtained by the optical fiber sensor to a ground computer for analysis processing, screening the hyperspectral images, extracting spectrum information in pixels of a region of interest and then comparing with an optical fingerprint library of substances in a laboratory for analysis so as to obtain chemical composition information of the target object;

at step 4, based on physical-mechanical property parameters of the soils at different depths, in combination with the hyperspectral images of the soils at the corresponding depths and the obtained chemical information of the soils, performing comprehensive classification of vertical direction on the soils.

In conclusion, the present disclosure has at least one of the following beneficial technical effects.

1. In the present disclosure, the hyperspectral images of the in-situ soil can be obtained in real-time, and on this basis, the chemical composition information of the soil can be obtained and then compared with the result of the static cone penetration test to perform analysis and verification, improving the accuracy of classifying the complex soil by using the static cone penetration test.

2. In the present disclosure, by replacing the camera lens in the conventional hyperspectral imaging device with the optical fiber bundle and using the light path improvement structure, it has a higher spectral resolution, more compact structure, and smaller volume, helping the integrated use in the confined space.

3. In the present disclosure, light adjustment and splitting are performed by using the optical fiber bundle and the composite structure of directional grating-prism-diffraction grating-prism; the light path has a simple structure and there are no movable parts, increasing the immunity to vibration and interference.

4. In the present disclosure, the in-built self-contained structure of the power supply and the wireless transceiver is used, eliminating the need of power supply and signal transmission cables, reducing the electric energy and information loss, and effectively improving the information obtaining quality and capability.

BRIEF DESCRIPTIONS OF THE DRAWINGS

Numerals of the drawings are described below: 1. splitter device, 2. measurement rod, 3. friction cylinder, 4. resistance strain gauge, 5. housing, 6. wireless transceiver, 7. light source, 8. optical window, 9. area array optical fiber bundle, 10. temperature sensor, 11. area array image sensor, 12. washer, 13. power supply, 14. data processing chip, 15. input fiber collimator, 16. stray-light-eliminating diaphragm, 17. directional grating, 18. splitter housing, 19. directional splitter device, 20. output fiber collimator, 21. optical fiber port, 22. charge coupling device, 23. optical fiber decoder, 24. data interface, 25. electrical interface, and 26. fixing clamp ring.

DETAILED DESCRIPTIONS OF EMBODIMENTS

The present disclosure will be further detailed below with the drawings 1 to 6.

Embodiment 1

Figure 1:
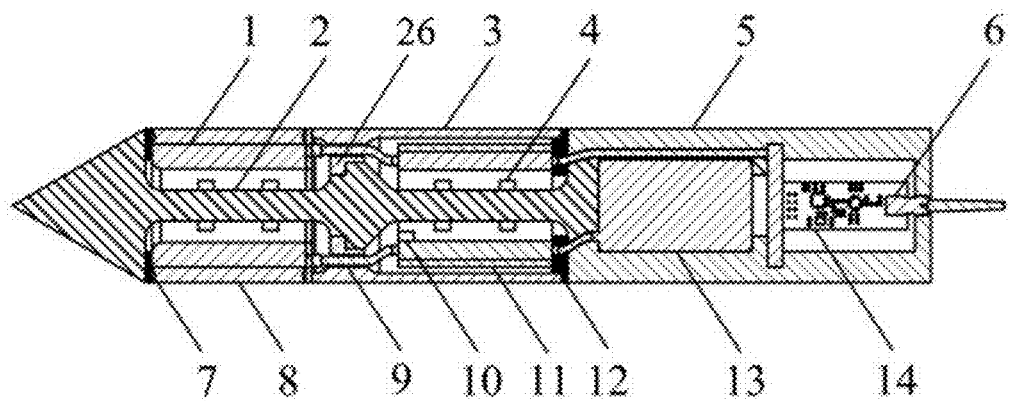
FIG. 1 is a schematic diagram illustrating an entire structure according to an embodiment of the present disclosure.

The embodiment of the present disclosure provides a static cone penetration test device incorporating hyperspectral imaging technology. With reference to FIG. 1, the static cone penetration test device incorporating hyperspectral imaging technology includes a cylindrical pressure-resistant housing 5, a friction cylinder 3 and an optical window 8 connected coaxially, where their outer sidewalls are flush with each other. An end of the optical window 8 is fixedly provided with a conical probe.

Figure 2:
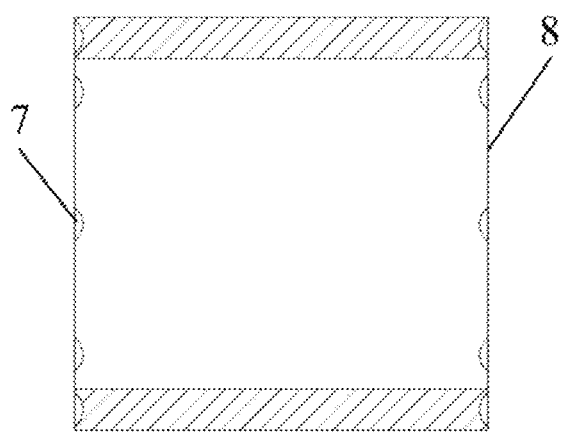
FIG. 2 is a sectional view illustrating an optical window according to an embodiment of the present disclosure.
Figure 3:
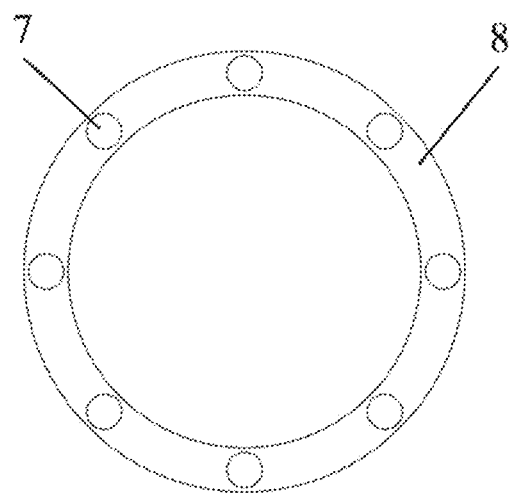
FIG. 3 is a right view illustrating an optical window according to an embodiment of the present disclosure.

With reference to FIGS. 2 and 3, multiple circular mounting holes are disposed at both ends of the axial direction of the optical window 8 respectively, and the multiple circular mounting holes are distributed equidistantly along a circumferential direction of the optical window 8. Light sources 7 are mounted in the mounting holes, where the irradiation angle of light sources 7 is adjustable. Light emitted by the light sources 7 can be penetrated through the optical window 8 into soil, a target object in the soil can reflect the light and then the reflected light can enter housing 5 through the optical window 8.

The optical window 8 is made of quartz, with its inner side surface and outer side surface both provided with an antireflection film, so as to reduce the reflection of the optical window 8 for the light emitted by the light sources 7. Furthermore, the outer side surface of the optical window 8 is provided with a sapphire coating film to reduce the wear of the optical window 8.

With reference to FIG. 1, a static cone penetration assembly is disposed inside the friction cylinder 3 to detect a resistance that the device suffers when the device is penetrated into the soil.

With reference to FIG. 1, an optical fiber sensor, a wireless transceiver 6, a data processing chip 14 and a power supply 13 are disposed of inside the housing 5. The optical fiber sensor is used to receive the reflected light of the target object and output information of two spatial dimensions and one spectral dimension. The wireless transceiver 6 is used to upload test data and receive control signals. The data processing chip 14 is used to analyze electrical signals output by the optical fiber sensor and send data to the wireless transceiver 6. The power supply 13 is used to supply power to the light sources 7, the optical fiber sensor, the data processing chip 14 and the wireless transceiver 6.

During detection, the present device is penetrated into the soil by using a penetration device and a detection rod. During a static cone penetration process, light emitted by the light sources 7 is penetrated through the optical window 8 into the soil and irradiated on the target object and then reflected, and the optical fiber sensor receives the reflected light and outputs spatial position and spectrum information of the target object within a planar imaging region.

The present disclosure is compact in structure and easy to use in an integrated way in a confined space, and also can obtain, in real-time, hyperspectral images of the in-situ soil; on the other hand, by the spectral information, chemical composition information of the soil can be obtained and then compared with a result of the static cone penetration test to carry out analysis and verification, improving the accuracy of classifying complex soil using the static cone penetration test.

With reference to FIG. 1, the static cone penetration assembly includes a measurement rod 2 disposed inside the friction cylinder 3 and multiple resistance strain gauges 4 fixedly connected on a circumferential side of the measurement rod 2. A conveying piece for conveying a force applied by the soil to the friction cylinder 3 to the measurement rod 2 is disposed inside the friction cylinder 3. The outer diameter of the friction cylinder 3 is identical to the maximum diameter of the conical probe. A cone angle, a conebottom sectional area of the conical probe and a surface area of the friction cylinder 3 are all in compliance with the requirements of GB50021-2009 Code for Investigation of Geotechnical Engineering and ASTM D3441-16.

Specifically, with reference to FIG. 1, measurement rod 2 includes an upper measurement rod, a middle-end head and a lower measurement rod fixedly connected coaxially, where the middle-end head has a larger diameter than the upper measurement rod and the lower measurement rod. The conveying piece is a fixing clamp ring 26, where an inner ring of the fixing clamp ring 26 is fixedly connected at the middle-end head and an outer ring thereof is fixedly connected on an inner sidewall of the friction cylinder 3.

With reference to FIG. 1, the resistance strain gauges 4 are mounted on circumferential sides of the upper measurement rod and the lower measurement rod. Four resistance strain gauges 4 are mounted on each of the circumferential sides of the upper measurement rod and the lower measurement rod, and four resistance strain gauges 4 are symmetrically distributed in pairs along an axis of the upper measurement rod or the lower measurement rod. The measurement direction of the resistance strain gauges 4 is in the axis direction of the measurement rod 2.

Furthermore, with reference to FIG. 1, a washer 12 is disposed between the friction cylinder 3 and housing 5. The washer 12 is made of a material having low rigidity and Poisson's ratio to prevent the washer 12 from bearing a pressure axially or radially or deforming.

When the present device penetrates the soil, the force applied by the soil to the friction cylinder 3 is conveyed to the measurement rod 2 by the fixing clamp ring 26, and the resistance of the resistance strain gauges 4 changes depending on the deformation of the measurement rod 2 to convert the resistance into an electrical signal, achieving measurement on the resistance.

With reference to FIG. 1, the optical fiber sensor includes an optical fiber array, a splitter device 1, an area array optical fiber bundle 9 and an area array image sensor 11 connected in sequence. An input end of the optical fiber array (not shown) is disposed on an inner side surface of the optical window 8, and an axial direction of an optical fiber end of the optical fiber array is perpendicular to the inner side surface of the optical window 8.

The light emitted by the light sources 7 is irradiated on the target object and then reflected into the optical fiber array through the optical window 8, and then through the optical fiber array into the splitter device 1. The splitter device 1 decomposes the composite light into discrete lights of different wavebands, and the discrete lights are then transmitted into the area array image sensor 111 through the area array optical fiber bundle 9 for signal processing.

Figure 4:
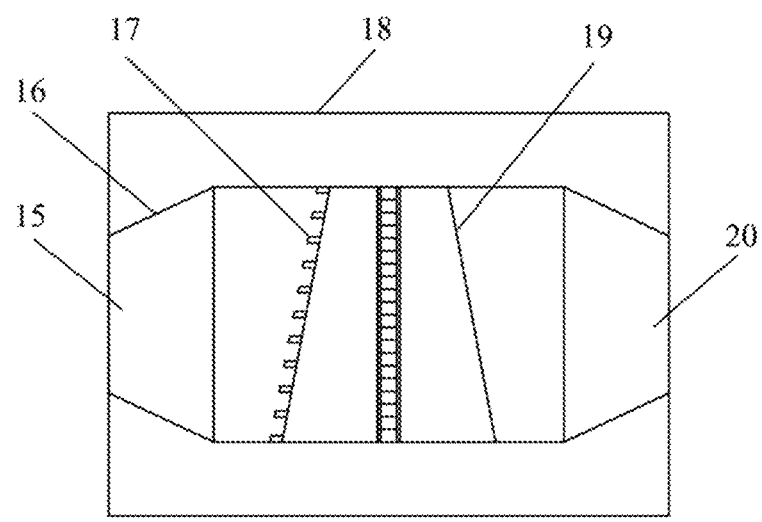
FIG. 4 is a sectional view illustrating a splitter device according to an embodiment of the present disclosure.

With reference to FIG. 4, the splitter device 1 includes a splitter housing 18, an input fiber collimator 15, a directional splitter device 19 and an output fiber collimator 20, where the input fiber collimator 15, the directional splitter device 19 and the output fiber collimator 20 are located in the splitter housing 18 and sequentially disposed along a light path. The input fiber collimator 15, the directional splitter device 19 and the output fiber collimator 20 are coaxial. A black light-absorbing coating is disposed on an inner sidewall of the splitter housing 18 and a stray-light-eliminating diaphragm 16 is disposed between the splitter housing 18 and the input fiber collimator 15.

Furthermore, the directional splitter device 19 is a composite structure of directional grating-prism-diffraction grating-prism, and a quartz protective layer is disposed at both sides of a directional grating 17 and a diffraction grating. The directional grating 17 can block the light non-paralleled to a light axis from entering and regulates a diverging light into a parallel light, and the diffraction grating decomposes the composite light passing through the directional grating 17 into several hundred discrete lights of different wavelengths.

The light sequentially runs through the input fiber collimator 15, the directional splitter device 19 and the output fiber collimator 20 such that the composite light is decomposed into discrete lights of different wavebands. Light adjustment and splitting are performed by the composite structure of directional grating-prism-diffraction grating-prism. The light path has a simple structure and there are no movable parts, increasing the immunity to vibration and interference. The black light-absorbing coating and the stray-light-eliminating diaphragm 16 can reduce non-imaging lights and improve the imaging effect.

With reference to FIG. 1, the area array optical fiber bundle 9 is penetrated through the fixing clamp ring 26. The area array optical fiber bundle 9 includes a rubber protective layer and multiple optical fiber threads which are of regularly-arranged structure. There is a one-to-one corresponding two-dimensional spatial position encoding information between an input end and an output end of the optical fiber threads. Furthermore, the surfaces of the optical fiber threads are coated with a high reflectivity material, and a light absorbent is filled between the optical fiber threads, so as to reduce a transmission loss of the light in the optical fiber threads. An antireflection angle is disposed at the input end and the output end of the optical fiber threads to reduce the unfavorable influence of the sectional reflection of the optical fiber threads on the imaging quality.

Figure 5:
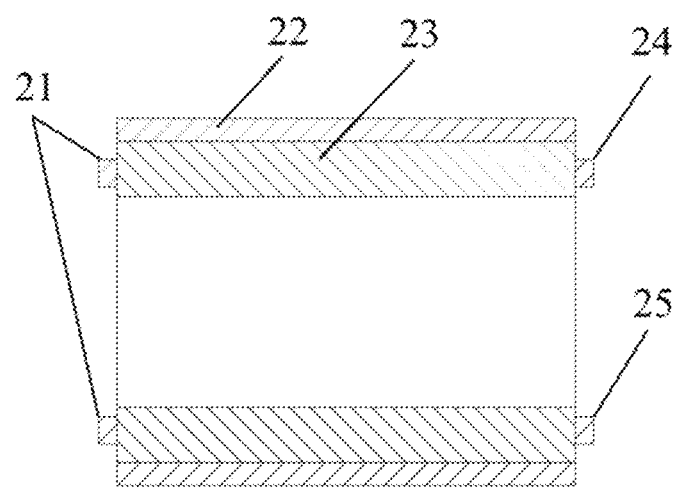
FIG. 5 is a sectional view illustrating an area array image sensor according to an embodiment of the present disclosure.
Figure 6:
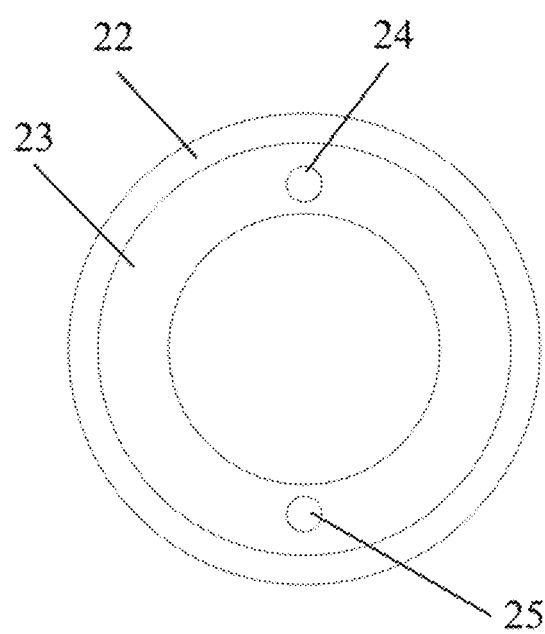
FIG. 6 is a right view illustrating an area array image sensor according to an embodiment of the present disclosure.

With reference to FIGS. 5 and 6, the area array image sensor 11 includes an optical fiber decoder 23 and a charge coupling device 22. The area array image sensor 11 is provided with an optical fiber port 21 which is connected with the output end of the area array optical fiber bundle 9 to receive an image encoding signal. The optical fiber decoder 23 is connected with the optical fiber port 21 to decode an input signal of the optical fiber port 21 into a two-dimensional optical signal.

The charge coupling device 22 is connected with the optical fiber decoder 23 to convert the decoded two-dimensional optical signal into an electrical signal. The charge coupling device 22 includes two spatial dimensions and one spectral dimension, where the spatial dimensions are used to output the spatial position information of the target object within the planar imaging region and the spectral dimension is used to output the spectrum information of the target object. The charge coupling device 22 is provided with an electrical interface 25 and a data interface 24.

The discrete lights output by the splitter device 1 enter the optical fiber decoder 23 through the area array optical fiber bundle 9 for decoding, and then the charge coupling device 22 performs analysis and processing on the optical signal, converts the optical signal into an electrical signal and outputs the spatial position information of the target object and the spectrum information of the target object within the planar imaging region.

The power supply 13 is connected with the light sources 7, the data processing chip 14 and the wireless transceiver 6 through cables. The power supply 13 is connected with the charge coupling device 22 through the electrical interface 25 to supply the desired power.

The data processing chip 14 is connected with the charge coupling device 22 through the data interface 24 to perform analysis processing on the electrical signal, obtain, by analysis, data body containing the spatial position and spectrum information of the target object, and upload the data body to a ground computer through the wireless transceiver 6.

The ground computer performs analysis processing on the uploaded data and outputs video, image and spectral feature information, and then compares the information with an optical fingerprint library of substances in a laboratory to obtain the substance chemical composition information and the like of the target object.

The implementation principle of the static cone penetration test device incorporating hyperspectral imaging technology in the embodiments of the present disclosure is as follows: during detection, the present device penetrates soil by using a penetration device and a detection rod. During a static cone penetration process, light emitted by the light sources 7 is penetrated through the optical window 8 into the soil and irradiated on the target object and then reflected, and the reflected light runs through the optical window 8, the splitter device 1 and the area array optical fiber bundle 9 into the area array image sensor 11, and thus the spatial position and spectrum information of the target object within the planar imaging region can be output.

The present disclosure is compact in structure and easy to use in an integrated way in a confined space, and also can obtain, in real-time, hyperspectral images of the in-situ soil; on the other hand, by the spectral information, chemical composition information of the soil can be obtained and then compared with a result of the static cone penetration test to carry out analysis and verification, improving the accuracy of classifying complex soil using the static cone penetration test.

Embodiment 2

The embodiment of the present disclosure provides a static cone penetration test method incorporating hyperspectral imaging technology, which is carried out by using the static cone penetration test device incorporating hyperspectral imaging technology mentioned in the embodiment 1. The method includes the following steps.

At step 1, detection and calibration are performed on the present device, the penetration device and the detection rod before a test; device testing and temperature calibration using temperature sensors are performed on the parameters of the resistance strain gauge such as an initial resistance R0, an initial length L0 and a resistance change amount K for each unit length of change; test and calibration are performed on the parameters of the upper measurement rod and the lower measurement rod such as a cross-section area A, a deformation modulus E and a Poisson's ratio u; the resistance strain gauges are mounted on the surfaces of the upper measurement rod and the lower measurement rod.

At step 2, the present device, the detection rod and the penetration device are sequentially connected and fixed. The verticality of the equipment is checked, and preliminary detection is performed on a nearby site.

At step 3, the detection rod and the present device are pressed into the soil at a constant speed by using the penetration device, where the pressing speed is 1.2 meters/second.

At step 4, a depth Z of an end head of the device is recorded in real-time, and an average value R1 of the resistances of all resistance strain gauges on the surface of the upper measurement rod and an average value R2 of the resistances of all resistance strain gauges on the surface of the lower measurement rod are detected; further, the hyperspectral images obtained by the optical fiber sensor are transmitted in real-time to the ground computer through the wireless transceiver for analysis processing.

At step 5, an end resistance and a lateral frictional resistance are calculated:

an acting force FU received by the upper measurement rod is calculated below:

$$FU=[(R1-R0)\cdot E\cdot A]/(u\cdot K\cdot L0)$$

an acting force FD received by the lower measurement rod is calculated below:

$$FD=[(R2-R0)\cdot E\cdot A]/(u\cdot K\cdot L0)$$

the acting force FU received by the upper measurement rod is a sum of the end resistance F1 and the lateral frictional resistance F2, which is calculated as below:

$$FU=F1+F2$$

the acting force FD received by the lower measurement rod is a difference between the end resistance F1 and the lateral frictional resistance F2, which is calculated as below:

$$FD=F1-F2$$

the end resistance F1 is calculated as below:

$$F1=[(R1+R2-2R0)\cdot E\cdot A]/(2\cdot u\cdot K\cdot L0)$$

the lateral frictional resistance F2 is calculated as below:

$$F2=[(R1-R2)\cdot E\cdot A]/(2\cdot u\cdot K\cdot L0)$$

At step 6, an empirical relationship between the end resistance F1/the lateral frictional resistance F2 and physical-mechanical property parameters of the soil is established; a change relationship and a curve of the end resistance F1/the lateral frictional resistance F2 versus the depth Z and a change relationship and a curve of the physical-mechanical property parameters of the soil versus the depth Z are recorded and drawn.

At step 7, the obtained hyperspectral images are screened to remove repeated images and those images with poor imaging quality and store representative high-quality hyperspectral images; in the valid hyperspectral images, a region of interest is selected to extract the spectrum information stored in the pixels of the region of interest, and then in combination with the test data such as optical fingerprint library of substances in the laboratory, the chemical information of the target object in the region of interest is obtained.

At step 8, based on the physical-mechanical property parameters of the soils at different depths Z, in combination with the hyperspectral images of the soils at the corresponding depths and the obtained chemical information of the soils as well as the region experiences and adjacent borehole data, comprehensive classification of vertical direction is performed on the soils.

The above are preferred embodiments of the present disclosure and shall not be understood as limiting the scope of protection of the present disclosure. Therefore, any equivalent changes made based on the structures, shapes and principles of the present disclosure shall all fall within the scope of protection of the present disclosure.

What is claimed is:

1. A static cone penetration test device incorporating hyperspectral imaging technology, comprising:
   a housing;
   a friction cylinder, coaxially connected with the housing;
   a static cone penetration assembly, disposed inside the friction cylinder to detect a resistance the device suffers when the device is pressed into a soil;
   an optical window, coaxially connected with the friction cylinder;
   light sources, mounted inside the optical window, wherein light emitted by the light sources is penetrated through the optical window into the soil, and a target object in the soil reflects the light and then the reflected light enters the housing through the optical window;
   wherein the static cone penetration assembly comprises a measurement rod disposed inside the friction cylinder and multiple resistance strain gauges fixedly connected on a circumferential side of the measurement rod; a conveying piece for conveying a force applied by the soil to the friction cylinder to the measurement rod is disposed inside the friction cylinder;
   wherein the measurement rod comprises an upper measurement rod, a middle-end head and a lower measurement rod fixedly connected coaxially, and the middle-end head has a larger diameter than the upper measurement rod and the lower measurement rod; the conveying piece is a fixing clamp ring, wherein an inner ring of the fixing clamp ring is fixedly connected at the middle-end head and an outer ring is fixedly connected on an inner sidewall of the friction cylinder; and the resistance strain gauges are mounted on circumferential sides of the upper measurement rod and the lower measurement rod;
   wherein inside the housing are disposed:
   an optical fiber sensor, configured to receive the reflected light of the target object and output information of two spatial dimensions and one spectral dimension;
   a wireless transceiver, configured to upload test data and receive a control signal;
   a data processing chip, configured to perform analysis processing on an electrical signal output by the optical fiber sensor and send data to the wireless transceiver; and
   a power supply, configured to supply power to the light sources, the optical fiber sensor, the data processing chip and the wireless transceiver, wherein the optical fiber sensor comprises an optical fiber array, a splitter device, an area array optical fiber bundle and an area array image sensor connected in sequence, the optical fiber array is disposed on an inner side surface of the optical window, and an axial direction of the optical fiber array is perpendicular to the inner side surface of the optical window, wherein the received light penetrated through the optical fiber array, the splitter and the area array optical fiber bundle in sequence, wherein the splitter device comprises a splitter housing, an input fiber collimator, a directional splitter device and an output fiber collimator, wherein the input fiber collimator, the directional splitter device and the output fiber collimator are located in the splitter housing and sequentially disposed along a light path; the input fiber collimator, the directional splitter device and the output fiber collimator are coaxial.

2. The static cone penetration test device according to claim 1, wherein a washer is disposed between the friction cylinder and the housing.

3. The static cone penetration test device according to claim 1, wherein the area array image sensor comprises an optical fiber decoder and a charge coupling device; the optical fiber decoder is connected with an output end of the area array optical fiber bundle to decode an image encoding signal into a two-dimensional optical signal; the charge coupling device is connected with the optical fiber decoder to convert the decoded two-dimensional optical signal into an electrical signal.

4. The static cone penetration test device according to claim 1, wherein a black light-absorbing coating is disposed on an inner sidewall of the splitter housing.

5. The static cone penetration test device according to claim 1, wherein a stray-light-eliminating diaphragm is disposed between the splitter housing and the input fiber collimator.

6. A static cone penetration test method incorporating hyperspectral imaging technology, which is carried out by using the static cone penetration test device incorporating hyperspectral imaging technology according to claim 1, wherein the method comprises the following steps:
   at step 1, performing device testing and calibration and mounting resistance strain gauges;
   at step 2, penetrating the device into the soil by using a detection rod and a penetration device;
   at step 3, recording a depth of an end head of the device in real-time, detecting a resistance of the resistance strain gauges and calculating an end resistance and a lateral frictional resistance; further, transmitting in real-time, by the wireless transceiver, the hyperspectral images obtained by the optical fiber sensor to a ground computer for analysis processing, screening the hyperspectral images, extracting spectrum information in pixels of a region of interest and then comparing with an optical fingerprint library of substances in a laboratory for analysis so as to obtain chemical composition information of the target object;
   at step 4, based on the physical-mechanical property parameters of the soils at different depths, in combination with the hyperspectral images of the soils at the corresponding depths and the obtained chemical information of the soils, performing comprehensive classification of vertical direction on the soils.

7. A static cone penetration test method incorporating hyperspectral imaging technology, which is carried out by using the static cone penetration test device incorporating hyperspectral imaging technology according to claim 2, wherein the method comprises the following steps:
   at step 1, performing device testing and calibration and mounting resistance strain gauges;
   at step 2, penetrating the device into the soil by using a detection rod and a penetration device;
   at step 3, recording a depth of an end head of the device in real-time, detecting a resistance of the resistance strain gauges and calculating an end resistance and a lateral frictional resistance; further, transmitting in real-time, by the wireless transceiver, the hyperspectral images obtained by the optical fiber sensor to a ground computer for analysis processing, screening the hyperspectral images, extracting spectrum information in pixels of a region of interest and then comparing with an optical fingerprint library of substances in a laboratory for analysis so as to obtain chemical composition information of the target object;
   at step 4, based on the physical-mechanical property parameters of the soils at different depths, in combination with the hyperspectral images of the soils at the corresponding depths and the obtained chemical information of the soils, performing comprehensive classification of vertical direction on the soils.

8. A static cone penetration test method incorporating hyperspectral imaging technology, which is carried out by using the static cone penetration test device incorporating hyperspectral imaging technology according to claim 3, wherein the method comprises the following steps:
   at step 1, performing device testing and calibration and mounting resistance strain gauges;
   at step 2, penetrating the device into the soil by using a detection rod and a penetration device;
   at step 3, recording a depth of an end head of the device in real-time, detecting a resistance of the resistance strain gauges and calculating an end resistance and a lateral frictional resistance; further, transmitting in real-time, by the wireless transceiver, the hyperspectral images obtained by the optical fiber sensor to a ground computer for analysis processing, screening the hyperspectral images, extracting spectrum information in pixels of a region of interest and then comparing with an optical fingerprint library of substances in a laboratory for analysis so as to obtain chemical composition information of the target object;
   at step 4, based on the physical-mechanical property parameters of the soils at different depths, in combination with the hyperspectral images of the soils at the corresponding depths and the obtained chemical information of the soils, performing comprehensive classification of vertical direction on the soils.

9. A static cone penetration test method incorporating hyperspectral imaging technology, which is carried out by using the static cone penetration test device incorporating hyperspectral imaging technology according to claim 4, wherein the method comprises the following steps:
   at step 1, performing device testing and calibration and mounting resistance strain gauges;
   at step 2, penetrating the device into the soil by using a detection rod and a penetration device;
   at step 3, recording a depth of an end head of the device in real-time, detecting a resistance of the resistance strain gauges and calculating an end resistance and a lateral frictional resistance; further, transmitting in real-time, by the wireless transceiver, the hyperspectral images obtained by the optical fiber sensor to a ground computer for analysis processing, screening the hyperspectral images, extracting spectrum information in pixels of a region of interest and then comparing with an optical fingerprint library of substances in a laboratory for analysis so as to obtain chemical composition information of the target object;

at step 4, based on the physical-mechanical property parameters of the soils at different depths, in combination with the hyperspectral images of the soils at the corresponding depths and the obtained chemical information of the soils, performing comprehensive classification of vertical direction on the soils.

10. A static cone penetration test method incorporating hyperspectral imaging technology, which is carried out by using the static cone penetration test device incorporating hyperspectral imaging technology according to claim 5, wherein the method comprises the following steps:

at step 1, performing device testing and calibration and mounting resistance strain gauges;

at step 2, penetrating the device into the soil by using a detection rod and a penetration device;

at step 3, recording a depth of an end head of the device in real-time, detecting a resistance of the resistance strain gauges and calculating an end resistance and a lateral frictional resistance; further, transmitting in real-time, by the wireless transceiver, the hyperspectral images obtained by the optical fiber sensor to a ground computer for analysis processing, screening the hyperspectral images, extracting spectrum information in pixels of a region of interest and then comparing with an optical fingerprint library of substances in a laboratory for analysis so as to obtain chemical composition information of the target object;

at step 4, based on the physical-mechanical property parameters of the soils at different depths, in combination with the hyperspectral images of the soils at the corresponding depths and the obtained chemical information of the soils, performing comprehensive classification of vertical direction on the soils.

* * * * *